United States Patent [19]
Hersh

[11] Patent Number: 5,906,811
[45] Date of Patent: May 25, 1999

[54] INTRA-ORAL ANTIOXIDANT PREPARATIONS

[75] Inventor: Theodore Hersh, Atlanta, Ga.

[73] Assignee: Thione International, Inc., Atlanta, Ga.

[21] Appl. No.: 08/884,282

[22] Filed: Jun. 27, 1997

[51] Int. Cl.⁶ .............................. A61K 7/22; A61K 7/16; A61K 31/095
[52] U.S. Cl. .................................. 424/54; 424/49; 604/58
[58] Field of Search .................. 128/200.23; 604/58; 514/901; 424/49

[56] References Cited

U.S. PATENT DOCUMENTS

| | | | |
|---|---|---|---|
| 4,648,393 | 3/1987 | Landis et al. | 228/200.23 |
| 4,790,305 | 12/1988 | Zoltan et al. | 127/200.23 |
| 5,667,791 | 9/1997 | Hersh et al. | 424/401 |

OTHER PUBLICATIONS

Abstract of Brilton et al Arch. Environ. Health 35(2) 1980. pp. 74–76.
Absract of Psarras et al Swedish Dental Journal (1994) 18(1–2) pp. 15–23.
Abstract of Eisenberg et al Caries Research (1990) 24(5) pp. 306–311.

*Primary Examiner*—Peter F. Kulkosky
*Attorney, Agent, or Firm*—Malcolm B. Wittenberg

[57] ABSTRACT

The combination of several synergistic antioxidants, enzymatic co-factors and amino acids in appropriate delivery vehicles employed in aerosol carriers, mist and pump oral sprays, solutions, such as oral irrigators, mouth rinses and mouthwashes, or gels and solid compositions as a means of preventing and ameliorating signs and symptoms and complications to the oro-pharyngeal cavity and mouth including buccal mucosa, gums and tongue and the upper respiratory tract from damage caused by free radical species induced by tobacco smoke, smokeless tobacco, ingested or chewed noxious, malodorous or harmful substances and other inhaled environmental pollutants and particulate matter, including tobacco to secondary smokers.

8 Claims, No Drawings

INTRA-ORAL ANTIOXIDANT PREPARATIONS

TECHNICAL FIELD OF THE INVENTION

The present invention deals with the combination of several synergistic antioxidants, enzymatic co-factors and amino acids in appropriate delivery vehicles employed in aerosol carriers, mist and pump oral sprays, solutions, such as oral irrigators, mouth rinses and mouthwashes, or gels and solid compositions as a means of preventing and ameliorating signs and symptoms and complications to the oro-pharyngeal cavity and mouth including buccal mucosa, gums and tongue and the upper respiratory tract from damage caused by free radical species induced by tobacco smoke, smokeless tobacco, ingested or chewed noxious, malodorous or harmful substances and other inhaled environmental pollutants and particulate matter, including tobacco to secondary smokers.

BACKGROUND OF THE INVENTION

The deleterious effects of tobacco abuse are well known and regulatory agencies as well as the public constantly react to these scientific and epidemiologic evidences. Tobacco is indeed a worldwide public health hazard accounting for significant morbidity and mortality. Although smoking places an abundant oxidant insult to the oro-pharynx and respiratory tract, plus the local existing atmospheric pollutants in that specific environ, evidence is that the oxidant burden is on the entire organism of the smoker, particularly development or enhancement of atherosclerosis, causing cardiovascular disease, chronic obstructive pulmonary disease and various forms of cancer, including carcinomas of the mouth, pharynx, esophagus and lung.

Tobacco is a substance consisting of the dried leaves and stems of the plant *Nicotiana Tabacum* which contains the drug nicotine, which is very addictive. The plant is native to North America but is now grown worldwide. Tobacco abuse has been identified as the single most preventable cause of disease, morbidity and mortality. Tobacco smoke contains many toxic chemicals and free radical species. There are three principal ways to consume tobacco: smoking, chewing and dipping and snuffing. 50 million Americans smoke and countless others are affected by tobacco smoke as secondary smokers. Children of smokers breathe this second-hand smoke and have more respiratory problems than children of non-smokers. Smokeless tobacco is used by as many as 12 million individuals and has a detrimental effect on the oral cavity plus systemic effects from buccal absorption of nicotine and other chemicals. Chewing looseleaf tobacco and "dipping" moist, ground snuff tobacco are common uses of tobacco without smoking. "Snuffing," that is, "snorting" dry powdered tobacco into the nasal passageways is rarely used in this country. Health risks from smokeless tobacco are still very significant and it is not a substitute for smoking.

Studies have estimated that tobacco smoke has over 3,000 different constituents, of which a number are toxic, some are carcinogenic and many generate free radical species. Most of these compounds have been identified in so-called mainstream and sidestream tobacco smoke. The former is that volume of smoke drawn through the mouthpiece of the tobacco product during puffing while sidestream smoke is that smoke emitted from the smoldering cigarette in between puffs. Although tar and nicotine are retained in the filter of cigarettes, this applies mainly to mainstream smoke, when comparing filter and non-filter cigarettes. Mainstream smoke emission is also markedly reduced both in low and in ultra low tar yield cigarettes. However, the emissions of toxic and carcinogenic components in sidestream smoke are not significantly reduced in filter cigarettes when compared to non-filter counterparts. Thus, sidestream smoke is a major contributor to environmental smoke, affecting both the smoker and their non-smoking counterparts, so called secondary smokers. The lower rates of consumption of cigarettes with high smoke yields has not reduced the indoor pollutants of carcinogenic substances and free radicals generating potential of tobacco smoke produced in sidestream smoke, albeit their diminished levels in mainstream smoke by smoking low yield tobaccos and filter cigarettes.

Cigarette smoke induces oxidative damage to lipids, DNA and proteins, particularly protein-SH groups for this smoke contains high levels of both free radicals and aldehydes, including acetaldehyde (ethanol), propanol and acrolein, as well as other deleterious molecules.

In U.S. Pat. No. 5,060,672 (Oct. 29, 1991) which is herein incorporated by reference, Irimi and co-workers disclosed an efficient filter for tobacco smoke. Their mechanical and adsorptive filtering component also provided chemosorptive properties to reduce aldehydes in the cigarette's smoke.

Tobacco, whether smoked as cigarettes, cigars or pipe or used as it is so-called smokeless or chewing modalities, causes common untoward effects in the oral cavity. Tobacco smoke has two chances to exert its deleterious effects in the mouth; when it is inhaled by the smoker and on its exit during exhalation. The American Lung Association states that chewing tobacco, whether one calls it snuff, a chaw, a plug, spit or smokeless tobacco is still a form of tobacco. The nicotine content is akin to cigarettes and this tobacco is etiologically responsible for oral cancer, just where it is chewed or "stored," in the mouth, cheek or gums.

Like cigarettes, evidence shows that cigars are also toxic and addictive. Cigar and cigarette smokers have a similar increased risk for oral and laryngeal cancers. While cigarette tobacco is generally flue cured with a resulting mildly acidic product, the slower curing methods for cigars render these mildly alkaline. At this pH, nicotine is more readily absorbed. Unlike cigarettes, cigars are less homogenous, and vary in size and nicotine content. Cigar smokers may spend an hour smoking a single large "Havana" although some actively inhale very little of this smoke; however, in non-inhalers, their nicotine levels may be elevated with no toxic co-absorption, as occurs in cigarette smokers. Cigar smokers also commonly hold an unlit cigar in the mouth, allowing further nicotine by local absorption. Thus, consumption of cigars may produce an equal or greater smoke burden of exposure and locally generate free radicals in the oral cavity which create deleterious effects and a risk of oro-pharyngeal disease. For cigars, as for pipe tobacco and smokeless tobacco, there is less available publicity and information for consumers than for cigarette smokers, although concomitant administration of synergistic antioxidant compositions of the present application may help prevent oral cancers and ameliorate oro-pharyngeal complications of tobacco abuse, whether from cigarettes, cigars, pipe or smokeless tobacco.

Cigarette smoke is divided into two phases, tar and gas-phase smoke. Cigarette tar contains high concentrations of free radicals. The most common oxidants include semi-quinone which is in equilibrium with hydroquinones and quinones, particularly in the viscous tar matrix. Many tar extracts and the oxidants, including the latter, are water soluble and reduce oxygen to superoxide radical which can dismutate to form $H_2O_2$. Importantly, glass-fiber type cigarette filters retain almost all of the tar particles that are larger than 0.1 micron. Thus, the filter acts as a trap for tars in cigarette smoke. There are an inordinately large number of free radicals, greater than $10^{15}$, in each puff in the gas-phase of cigarette smoke. While the oxidants in tar are stable, those organic radicals in the gas phase smoke are reactive carbon and oxygen centered radicals with extremely short half lives. Interestingly, concentrations of free radicals are maintained at high levels for more than 10 minutes and tend to increase as tobacco smoke is aged. It is thus considered that these gas phase smoke oxidants are in a steady state as they are both continuously formed and destroyed. The latter reactions are similar to those noted to occur in smog, pointing to the extra noxious stimuli to primary and secondary smokers in polluted atmospheric environments. Although the best protection from cigarette smoke oxidant damage is cessation of smoking with personal and "environmental" abstinence, antioxidant protection is rendered by oral solutions, sprays and aerosol administration, as taught by the present disclosure, and by supplemented dietary means, as suggested by some clinical investigations. These oral sprays and inhalatory measures would ameliorate and delay putative tobacco oxidant damage in smokers and their nearby non-smoking neighbors, as well as for those who use chewing (smokeless) tobaccos.

In addition to the above, in other in vitro studies gas phase cigarette smoke was assessed in its filtered and whole (unfiltered) states for oxidative effects on human plasma. Investigators noted the prevalence of lipid peroxidation in plasma after exposure to the gas-phase smoke, but not to the whole cigarette smoke. The reaction of lipid peroxidation did not commence until the endogenous ascorbic acid had been consumed, that is, vitamin C was oxidized completely. It was noted that cigarette smoke exposure caused oxidation of plasma protein thiols (methionine and cysteine amino acid linkages) and low density lipo-proteins. It was concluded that lipid peroxidation induced by the oxidants of gas phase smoke leads to changes in the lipoproteins associated with atherogenesis. As noted in this disclosure, the synergistic effect of reduced glutathione, selenomethionine and ascorbic acid or an ascorbic acid derivative are beneficial to combating tobacco oxidants and both ameliorating and delaying the effects of tobacco smoke on the oro-pharynx and the upper respiratory mucosa.

Cells subjected to oxidative stress may severely affect cellular function and cause damage to membrane lipids, to proteins, to cytoskeletal structures and to DNA. Free radical damage to DNA has been measured as formation of single-strand breaks, double-strand breaks and chromosomal aberrations. Cells exposed to ionizing radiation and cigarette smoke have also been demonstrated to have an increased intracellular DNA damage, a precursor of mutations and development of malignancies.

Macrophage cells and neutrophils have their phagocytic activity associated with the so-called "respiratory burst" reaction, which is dependent on plasma membrane NADPH oxidase activity. The resulting oxygen radicals may then be transformed to $H_2O_2$ by superoxide dismutase. Investigators have shown that smokers have a higher "respiratory burst" reaction of alveolar macrophages and peripheral neutrophils than non-smokers and the former also have higher incidence of oral and respiratory signs and symptoms than non-smokers. It was determined that there is a decrease of the effect of this "respiratory burst" reaction in smokers supplemented with oral mega doses of antioxidants. The intra-oral and inhalatory preparations of the present invention with synergistic antioxidants are thus beneficial to primary and secondary smokers.

Because of the oro-pharynx's access to the environment, like the skin to oxygen and ultraviolet radiation, the structures of the oral cavity may be damaged by inhaled, ingested or chewed noxious substances and gaseous and particulate materials, especially in both active and passive smokers, as well as injuries by systemic xenobiotics and by endogenous processes, such as inflammatory reactions. Reactive oxidizing species, as induced by inhaled tobacco smoke, ozone and nitrous oxide are important factors in generating free radicals and inducing inflammatory reactions. As in other tissues, antioxidant enzymes exist in the oro-pharynx and include superoxide dismutase (SOD), which converts superoxide to hydrogen peroxide and catalase which reduces hydrogen peroxide to water. This reaction may also be catalyzed by selenium as a cofactor to the enzyme glutathione peroxidase using reduced glutathione (GSH) as a substrate. GSH-peroxidases may also reduce lipid peroxides to the corresponding alcohols also using GSH.

Glutathione, a sulphur containing tripeptide (L-gamma-glutamly-l-cysteinel-glycine) is the most abundant non-protein thiol in mammalian cells and is recognized as the primordial antioxidant. Glutathione, in its reduced form, known as GSH, acts as a substrate for the enzymes GSH-S-transferases and GSH peroxidases (with selenium cofactor) that both catalyze the reactions for the detoxification of xenobiotic compounds and for the antioxidation of reactive oxygen species and other free radicals. GSH synthesis takes place in two steps:

(1) An initial rate limiting step catalyzed by gamma glutamyl cysteine synthetase to form gamma glutamyl-cysteine.

(2) Glutathione synthetase catalyzes the reaction between glycine and glutamylcysteine to form GSH.

Intracellular stability is conferred to GSH by the gamma glutamyl bond's resistance to intracellular peptidases. This bond may be cleaved by gamma glutamyl transpeptidase which is usually located on the external surface of cell membranes. Its activity is high in the kidney, where GSH is subject to renal clearance by tubular cells and by this transpeptidation reaction, resulting in urine excretion or retransport to plasma as the constituent amino acids, glutamine, cysteine, and glycine. In this pool, along with nutritionally derived amino acids from digestion and small bowel absorption, these amino acids are available to the liver for GSH synthesis. The liver and lung also export GSH in its oxidized form denoted as GSSG, which is produced when peroxides are detoxified by GSH peroxidase. GSSG is recycled back to the reduced form, GSH, by glutathione reductase in a reaction with NADPH.

The ubiquitous glutathione plays a vital function in maintaining the integrity of the reactive oxygen species-free radical sensitive cellular components. This is accomplished through its direct role as an antioxidant, in its reduced (GSH) form, as well as a cofactor as aforementioned. In cells, GSH concentrations for antioxidant activity are maintained in equilibrium by the enzyme glutathione reductase. Under states of GSH depletion, including malnutrition and severe oxidative stress, cells may then become injured from excess free radical damage and die.

Other non-enzymatic molecules playing an antioxidant role include the ascorbates (vitamin C) which, as free radical scavengers, also react with oxidized glutathione (GSSG) and reduce it to GSH. Also, in the lipid membrane of the cells, the hydrophobic alpha-tocopherols (vitamin E) act synergistically with vitamin C to inhibit lipid peroxidation, as may be induced by cigarette smoke, by actively scavenging lipid peroxides and other radicals.

Various studies have correlated the importance of oxidant stress to various organs resulting from tobacco smoke and other noxious environmental factors and thus continue to exert a toll on the public health of all countries. Significant morbidity and mortality result from smoking tobacco from cigarettes, cigars, and pipes and local oral pathology from chewing tobacco. Epidemiologic studies have strongly implicated tobacco in the pathogenesis of atherosclerosis and various malignancies, including oro-pharyngeal and respiratory tract neoplasias. Chronic cigarette smoking is associated with appearance of free radicals inducing oxidative damage. Measurement in blood, urine and tissues of various antioxidants or of by-products of free radical metabolic processes are supportive of tissue oxidant damage in the pathogenesis of various diseases associated with tobacco smoking and environmental pollutants.

In the oro-pharynx, cigarette smoke also accelerates the production of reactive oxygen species by recruiting local neutrophils and activation of phagocytic cells in response to the noxious agents. Attack by cigarette smoke and free radicals upon plasma proteins may be measured by carbonyl assay and by loss of enzyme activity and SH groups. Researchers have shown that whole and gas phase cigarette smoke elicit formation of carbonyl in human plasma, which is particularly inhibited by GSH. In contrast, exposure of human plasma to gas phase but not to whole cigarette smoke produces oxidative damage to lipids.

Leukoplakia, a tobacco induced white patch on the buccal mucosa, as found in smokers, is a localized irritation due to direct contact of smoked or smokeless tobacco and it is directly related to the frequency and years of tobacco abuse. Although leukoplakia is a benign oral lesion, it has a malignant potential, requiring a biopsy of the lesion to rule out cancer. Leukoplakia may regress or resolve completely when use of tobacco products is discontinued. Adequate oral examinations by primary physicians and dentists is paramount to reduce smoke induced mouth and teeth pathology.

In addition, tobacco contributes to other oral symptoms or pathologies of the mouth and teeth. Tobacco may cause halitosis, may numb the taste buds, and interfere with the smell and the taste of food. It may stain teeth and contribute to dental caries. Smokers have more dental tartar (calculus) than non-smokers. Tobacco is associated also with destructive periodontal (gum) disease and tooth loss. Acute necrotizing ulcerative gingivitis ("trench mouth") is a destructive, painful inflammatory condition occurring mainly in cigarette smokers. Swelling of the nasal and sinus membranes have also been associated, purportedly, in individuals who are "allergic" to tobacco smoke.

Besides leukoplakia, another generalized whitish hue on the buccal mucosa represents the entity of oral submucous fibrosis. This disease occurs mainly in India and is a chronic, progressive premalignant condition. The etiology is chronic chewing of tobacco or areca nut or both. The fibrosis results in restriction of mouth opening and involves the palates, tonsillar fossa, buccal mucosa and underlying muscle. Associated with this condition is also oro-pharyngeal carcinomas, also with a high frequency in India and associated in 70% of cases with chewing tobacco. Smokeless tobacco and areca nut usage is also common in Pakistan, Bangladesh and Java and in these and Indian immigrants to the United States and United Kingdom.

Over 30,000 new cases of cancer of the oral cavity are diagnosed annually, accounting for two to four percent of all new cancers. Oral cancer kills 8,000 patients each year and only half of cases diagnosed annually have a five year survival. The great majority of these patients are users of tobacco products. Other risk factors include alcohol abuse, nutritional deficiencies and poor oral hygiene.

Research has recently linked benzopyrene, as in cigarette smoke, with mutations to the human P53 gene leading to oral and respiratory malignancies. Notably, 3, 4-benzopyrene is present in polluted atmospheres of large cities such as Los Angeles, Mexico City, and London, emanating as an exhaust product of motor traffic, especially diesel engines. Breathing contaminated air with high concentrations of this compound, particularly under foggy conditions as in London, provides more than 100 times as much of this putative mutagen than for a heavy cigarette smoker. Thus, the use of the present invention as taught herein would be most beneficial to citizens, particularly if they are also smokers, of congested cities with much traffic and with smog and fog. This provides to the individual another protective measure to such free radicals and mutagens generated in their bodies, not withstanding important measures to decontaminate the atmospheric pollutants and public health and personal efforts at tobacco cessation.

Cigarette filters "trap" nicotine tars but not the gas phase compounds. Epidemiologic studies have been done in various countries to show the differential effects of tar content, amount of cigarettes smoked, type of tobacco smoked, and use of filters on oro-pharyngeal and pulmonary cancer risk in cigarette smokers.

Cigarette smoke has untold effects through free radicals and other mechanisms of affecting other organs, such as the skin. Dr. Douglas Model of England in 1985 added to the medical lexicon the term "smoker's face" from a study with pictures of 116 cases and suitable non-smoking controls. Akin to photodamage, those with smoker's face appear older and have more wrinkles. They also have a greater frequency of cancers of the lips and mouth.

Recently, sales of cigars have risen, partly due to their gaining popularity with women and the advent of the female friendly "cigar bar." Evidence, however, exists that cigar carcinogenic particles exceed those of three cigarettes and the level of carbon monoxide is 30 times greater. Fumes from cigars are of greater consequence to secondary smokers. Epidemiologic studies reveal greater frequencies of heart disease, emphysema, and cancers of the mouth and pharynx in cigar smokers when compared to matched non-smokers.

There are a number of preparations on the market as dentifrices, gels, breath fresheners and mouthwashes and oral rinses to protect the mouth and teeth from the effects of chewed or smoked tobacco. Cigarette tar may deposit on the teeth, gums, tongue and other surfaces of the oral cavity of smokers. Tobacco tar, a dark, oily, viscid blend of polycyclic aromatic and aliphatic hydrocarbons, is produced in cigarettes, cigars, or pipe smoke by the burning of the tobacco. The smoker inhales the tar and other tobacco smoke combustion products are sucked into the oral cavity and respiratory passages. The smoke is then exhaled, passing a second time through the mouth of the smoker, anew depositing tar. This causes discoloration of the teeth and other oral surfaces. Not only may there be smoker's "bad breath" but also tooth decay and gum disease. Smokeless tobacco is equally locally deleterious. Food particles, oils and other substances may also be deposited on mouth surfaces. The tars and mainstream smoke will elicit free radical and inflammatory responses in the mouth and other mucosal surfaces. The antioxidants and reparative preparations of this invention may be prepared as oral and dental compositions as well as with optional added ingredients that are also breath fresheners, fluorides, anti-microbials, and solubilizers of tars and essential oils. Most of the dental products used as "anti-tobacco" are in the form of toothpastes and gels.

Diamond patented a combination of non-ionic and anionic surfactants with at least one essential oil as dental and oral preparations for smokers for solubilizing and removing tobacco tars as well as onion and garlic essential oils. U.S. Pat. No. 5,514,366 (May 7, 1996), herein incorporated by reference, teaches complimentary uses of the preventive and reparative effects of the present invention.

GSH has been shown to have multiple functions in detoxification and its depletion in extracellular fluids and cells is associated with an increased risk of chemical toxicity. Although there are large variations in dietary sulphur amino acid content, these variations do not correlate with GSH levels in the blood plasma pool. These GSH levels, however, do vary with age, race and gender of human subject and with dietary habits and intakes. Investigators have reported that extracellular pools of GSH, including plasma, respiratory tract lining fluid and oral and small intestinal lumen are GSH vital protectants against chemically induced injury. These would include the chemicals in tobacco smoke and other environmental pollutants as well as chemicals in smokeless tobacco preparations and other chewable or orally ingested substances. The aforementioned pools, through GSH and related synergistic antioxidants, as proposed in the present invention, detoxify chemicals extracellularly, supply GSH and its precursor amino acids to cells and protect the extracellular surface of the plasma membrane from damage. Alterations in GSH status could thus alter this regulatory function by GSH and thereby lower the threshold for chemically induced cell death by apoptosis, making GSH both a useful protectant to and biomarker for risk from a variety of single or mixtures of deleterious chemicals, such as in various types of tobacco.

Some mammalian cells are able to absorb intact the tripeptide glutathione. It may also be synthesized by some organs, particularly the liver. Various scientific papers have addressed a method for proper replacement of glutathione, particularly to increase cellular levels in glutathione depleted states. Certain diseases cause glutathione depletion from interaction endogenously with metabolic intermediates, the various deleterious free radical species. Labeling glutathione, at the intracellular level as the "antidote physiologically appointed to the neutralization and thus detoxification, by the formation of covalent bonds, of highly reactive toxic substances of endogenous or exogenous origin," Pilotto and coworkers patented dipeptide compounds with pharmaceutical properties to replete the body's glutathione levels. Their U.S. Pat. No. 4,761,399 dated Aug. 2, 1988, teaches raising glutathione levels by various routes, including oral, inhalation and parenteral methodologies. Meister, in U.S. Pat. No. 4,710,489 issued Dec. 1, 1987 teaches new molecules to increase cellular levels of glutathione. The invention of the '489 patent deals with using pure alkyl mono-esters of glutathione, wherein the ester is a glycine carboxylic acid. These molecules may be administered orally or by injection.

It is thus an object of the present invention to provide various compositions and methods of employing such compositions for preventing and ameliorating signs and symptoms and complications to the oro-pharyngeal cavity and mouth including buccal mucosa, gums, teeth and tongue as well as the upper respiratory tract as a result of tobacco oxidants and other gaseous and particulate matter pollutants.

These and further objects will be more readily appreciated when considering the following disclosure and appended claims.

SUMMARY OF THE INVENTION

The present invention is directed to the use of synergistic antioxidants employed in intra-oral and aerosol delivery systems to prevent and ameliorate free radical damage induced by smoking to the oro-pharynx and upper respiratory tract. The components supplied by solid compositions, intra-oral sprays and aerosol inhalation through various states of the art delivery methods include reduced glutathione, selenium as an element or as a selenoamino acid, like selenomethionine, and the sulphur containing amino acids L-cysteine or N-acetyl-L, cysteine and/or L-methionine, ascorbic acid and/or its derivatives, alpha-tocopherols and/or its derivatives. Depending on the target organ and the additional disease states or conditions encountered, other antioxidants or molecules may be included in these intra-oral compositions. These include but are not limited to the enzyme superoxide dismutase, vitamin A and/or beta carotene, zinc and fluoride compounds, bronchodilators, expectorants and other constituents as clinically indicated.

DETAILED DESCRIPTION OF THE INVENTION

Antioxidants have been found to inhibit all stages of carcinogenesis whereas other antioxidants are more specific and thus more effective against tumor initiation or promotion or tumor progression. Glutathione and selenium have been shown to play prime roles in protection of carcinogenesis and also in preventing other cancers, when selenium is taken orally thereby replenishing selenium body stores.

Likewise, glutathione, inhibits carcinogenesis, and indeed when its concentration is suppressed by chemicals so that glutathione levels are significantly lowered, chemical carcinogenesis is enhanced and progression of tumor numbers and tumor size increases. Reducing the intracellular levels of GSH in cells increases their sensitivity to oxidant damage. Studies have shown that increases in intracellular GSH are beneficial. An L-cysteine delivery agent not only enhanced endothelial cell GSH concentration, but also protected these cells from damage from endogenous hydrogen peroxide. This preventive role of GSH is of significant biologic value. Without being bound to any particular theory, it is noted that reduced glutathione is employed in protecting cells against oxidative stress by itself being oxidized. Thus, L-glutathione must act in combination with other enzyme systems in order to be reduced so that it may renew its role as a free radical scavenger. GSH functions also coordinately with the enzyme glutathione peroxidase which requires selenium as a cofactor to exert its biologic antioxidant function. Selenium compounds have been shown to scavenge oxygen-centered radicals in vivo with reduced glutathione through glutathione peroxidase. It is believed that selenium-GSH peroxidase catalyzes toxic hydrogen peroxidase in the presence of reduced glutathione. This reaction reduces glutathione to oxidized glutathione GSSG. In turn, the GSSG is reduced back to GSH by the enzyme GSH reductase thereby maintaining abundant cellular GSH to scavenge free radicals anew.

In summary, the major functions of reduced glutathione (GSH) in protection against lipid peroxidation are related to three types of reactions, all inter-related and synergistic in combining non-enzymic scavengers and enzymic and dietary provided antioxidants.

1. GSH with selenium co-factor glutathione peroxidases eliminate toxic peroxides.

2. GSH reduces oxidized forms of vitamin C which, in turn, maintains vitamin E in its reduced form promoting its metabolic functions. Thus, GSH supports the free radical reductions and free radical chain-terminating functions of the two nutrient antioxidants, vitamins C and E.

3. GSH functions through glutathione S-transferases to detoxify reactive aldehydes created during the process of lipid peroxidation.

As noted too, some cells have sodium dependent up-take systems for GSH, allowing cells to use both exogenous GSH and endogenously synthesized GSH, thereby enhancing a cell's ability to survive oxidative and free radical species damage. In this fashion, extra-cellular GSH also protects cells' survival.

Investigative. studies have shown that cells' viability correlates best with content of GSH in mitochondria. In the absence of GSH, lipid peroxidation is uncontrolled and leads to cell injury and death. Conversely, GSH protects cells from the ravages of free radicals, working synergistically with the antioxidant enzymes and the dietary vitamin antioxidants.

In a most preferred aspect of the present invention, the aforementioned oral or inhaled pharmaceuticals, amino acids and active antioxidant containing composition has a formulation for total daily consumption to include recommended daily allowances of reduced L-ascorbic acid, tocopherols, and other vitamins. In addition to L-glutathione, the preferred selenium dosage is approximately at least 10 mcgm of elemental selenium per day most preferably 25 mcgm per day. This may also be used as selenomethionine, which is commercially available in a 0.5% trituration with dibasic calcium phosphate. This fine powder contains from 5,000 to 5,300 mcgm of selenium per gram of the selenomethionine preparation. The compositions may also have about 30 IU of D,L-alpha tocopherol and about 1000 mcgm of vitamin A, as the retinol equivalent or 5,000 units as vitamin A with a range of 20–40% beta carotene. These are recommended daily allowances and these active ingredients may be administered in oral liposomes, either each encapsulated alone or in combinations. Knight and co-workers in U.S. Pat. No. 5,049,388 (Sep. 17, 1991), incorporated herein by reference, disclosed small particle aerosol liposomes. These particles had diameters less than 5 microns. Medications were combined with the liposomes such that the drug or active ingredient interacted with the liposome membrane.

The aforementioned compositions may be particularly useful in the prevention and treatment of tobacco smoke or other gaseous or particulate matter exposure, including buccal damage from chewing tobacco. They represent a delicate balance of ingredients which serve not only to reduce the number of free radicals but also to inhibit the tissular metabolic oxidation. The more preferred formulations in accordance with the present invention also enhance the performance of the composition by recycling certain antioxidant ingredients in the formulation after these are absorbed and by offering the formulation allowing for long term use. These compositions when provided in sufficient dosage over a period of time may be useful in the treatment and the prevention of the damage caused in the oropharynx and upper respiratory tract, by exposure to tobacco smoke, smokeless tobacco and other environmental pollutants.

Glutathione and selenium act synergistically in vivo as they are both constituents of the same enzymatic system. GSH serves as a specific donor substrate while selenium, provided from alimentary sources or locally from topically administered preparations of selenium, selenoamino acids or selenium yeast extract, provides the prosthetic group of GSH peroxidase. The glutathione and selenium antioxidant functions are intrinsically related since by keeping a peroxidase in action, the GSH and selenium, contribute to the removal of the dismutation product of free oxygen radicals, namely, hydrogen peroxide. in a broad sense, GSH and selenium modulate free radical chains initiated or sustained by hydroperoxides. Selenium is used in the present invention for its role as an antioxidant as well as its anticarcinogenic and antimutagenic properties. Thus, selenium-glutathione complex may lower the level of potentially damaging peroxide radicals that are generated from various carcinogenic promoting chemicals, including tar phase and gas phase tobacco smoke inhaled by-products, particularly sidestream smoke.

Glutathione peroxidase, a group of water soluble enzymes, also catalyze the destruction of both aqueous and membrane-bound hydroperoxides. In dietary selenium deficiency, these enzyme levels are markedly decreased resulting in severe free radical damage to the tissues so involved. The other related antioxidant systems cannot make up for depressed local activity of selenium and selenium dependent enzymes. Thus, the importance of providing selenium in these intra-oral antioxidant preparations, as well as ascertaining adequate nutritional supplements. Selenium may be provided as a selenoamino acid, like selenomethionine, as such, is protected in oral lipsomes.

L-ascorbic acid (vitamin C) or its derivatives can be employed in these compositions primarily for their antioxidant activities. Stabilized vitamin C is employed so that it does not lose its physiological reducing activities because of its high susceptibility to oxidation. The minimum daily requirement for adults has been established. It appears, however, that cigarette smokers need supplemental vitamin C. Vitamin C, as an antioxidant, has been employed in vitamins, beverages, foodstuffs, pharmaceuticals and cosmetic preparations. Vitamin C has also been used for the prevention of viral diseases and a preventative by its anti-oxidant properties of development of cutaneous pre-malignant lesions and malignant tumors. Sakai, et al in U.S. Pat. No. 5,508,390 (Apr. 16, 1996) have outlined uses of an L-ascorbic acid. Such stabilized vitamin C is used as an additive in various preparations. The emphasis of this preparation of ascorbic acid is in its stabilizing and reducing function. Todd, Jr., in U.S. Pat. No. 5,084,293 (Jan. 28, 1992), describes a method of using "activated" ascorbic acid preparations with antioxidant compositions. These include anhydrous compositions to embody propylene glycol or non-ionic surface-active agents to provide vitamin C with increased antioxidant activity in fats, oils, and carotenoids.

Vitamin C, ascorbic acid, plays a major role in human metabolism. As an antioxidant, it protects the skin from free radical damage induced by radiation, tobacco smoke, and other inhaled or swallowed environmental pollutants. Vitamin C promotes collagen synthesis, tissue repair and wound healing. Vitamin C also renders important protection against damaging chemicals associated with cigarette smoking, including nicotine, carbon monoxide, nitrogen oxides, nitric acid gas and others. Although ascorbic acid may be reduced in this scavenging role, the ascorbate radical may then be removed by the NaDPH enzyme systems as sources of reducing molecules. Thus, vitamin C may be recycled to abate or lessen the process of lipid peroxidation by its synergistic function with others. Markham in U.S. Pat. No. 4,822,891 refers to the oral administration of vitamin C to demonstrate its free radical attributes. Others have shown that chronic tobacco smokers had higher urinary levels of 8-EPI-prostaglandin F2A than non-smokers. Oral supplementation with vitamin C suppressed urinary levels of this metabolite, suggesting a reduction of oxidant stress in these subjects.

Cigarette smokers often have lower plasma levels of ascorbic acid than matched non-smoking controls. Clinical and investigative evidence suggests that smokers may have a higher ascorbic acid requirement and that supplementing dietary vitamin C may be protective to the smoker. In vitro studies have shown that antioxidants and reducing substances may prevent the removal of elastase inhibitor capacity induced by cigarette smoke.

In U.S. Pat. No. 4,525,341 (Jun. 25, 1985) which is herein incorporated by reference, Delhi introduced a method of administering vitamins to an air breathing mammal in an aerosol. Delhi included all those known vitamins and complex molecules with biological activity, namely, vitamin A and beta-carotene, vitamin B complex, and vitamins C, D, E and K. The liquid carrier depended on solubility of the vitamins, since A, D, E, K are fat soluble. He included the option of using breath fresheners and flavorings as known in this industry. The vitamin preparations are sprayed into the nose or mouth for local buccal mucosal absorption, with some part being swallowed with saliva for subsequent intestinal absorption, as in vitamins taken as liquid or solid (tablet, capsules, chewable) preparations. "Aerosol" definition included both colloidal suspension of liquid droplets in a gaseous carrier, simple temporary suspension of these droplets in the carrier, such as commonly used as "atomizers" in dispensing perfumes, colognes, and breath fresheners, wherein the liquid phase is reduced to a fine spray. In this patent, these vitamins by nasal or oral routes were proposed as a spray administration as dietary supplements to replace or complement vitamin preparations commonly given by oral or parenteral routes.

Other components were also investigated as being useful in practicing this invention, for example, the sulphur containing amino acid cysteine is one of the three amino acid constituents of the tripeptide antioxidant glutathione. Studies have shown that cysteine and cysteine derivatives, as recited in U.S. Pat. No. 4,910,222 by Puricelli, have liquefying and expectorating properties. These compounds may be administered by the oral route as a solid (capsules), or as a liquid (emulsions) and by aerosol sprays.

Vitamin A is an essential nutrient. Relative vitamin A deficiency may adversely affect the skin and mucous membranes, including the mucosa of the oral cavity. These alterations are reversible on repletion with vitamin A or one of its derivatives. U.S. Pat. No. 5,556,611 (Sep. 17, 1996), which is herein incorporated by reference, teaches a method for administering vitamin A by aerosol inhalants.

Xylitol, the sweetest of all bulk sugar substitutes, tastes like sugar, leaves no aftertaste, and has 40% less calories than sugar. A caloric value of 2.4 kcal/gram is accepted for nutritional labeling. This five carbon sugar alcohol has a negative heat of solution which causes a cooling effect when it dissolves in the mouth, particularly concomitantly using mint flavors. When sugars are ingested, the micro-organisms in the mouth ferment the sugars with a consequent drop in pH, even to a low pH of 4. When the contents in the mouth are acid, there is demineralization of tooth enamel. Stimulated flow of alkaline saliva is then necessary to return the pH in the mouth to normal levels. Thus, use of xylitol reduces susceptibility to dental caries by helping to remineralize affected teeth and by inhibiting demineralization of healthy teeth. Studies have also shown that adults chewing xylitol gum or xylitol/sorbitol gums or mouth rinses develop significantly less dental plaque than controls chewing sucrose gums. Their dental plaque too showed an improvement in the ability to resist any drop in pH. In the xylitol groups, studies show that xylitol inhibits the growth of various oral cariogenic bacteria, particularly those of Streptococcus mutans.

Although the susceptibility to dental caries is influenced by various factors including diet and eating patterns, tooth surface and salivary rates are also important. The resistance of the enamel and dentine may be increased by regular exposure of the teeth to fluorides systemically. This is accomplished via drinking water and fluoride tablets or topically via toothpaste, gels and mouthwash. Various studies have demonstrated that consumption of even small quantities of xylitol enhances the beneficial effects of existing fluoridation program, resulting in reduction in new caries. Similar trends have been observed when xylitol is applied topically such as a mouth rinse.

When the present preparations are in the form of oral sprays, gels, toothpaste, mouth wash, gargles, rinses or oral irrigators, flavorings may be added to these compositions, as per the state of the art in these respective industries. Flavors may be based on oils of spearmint and peppermint. Other flavoring materials may include menthol, clove, cinnamon, wintergreen, citrus fruits, eucalyptus, aniseed and others commercially available for these flavoring purposes.

Flavors may range in concentrations depending on the product from about 0.1 to about 6.0% by weight of the total composition.

When the products are in a form of gel, bicarbonates may be present in the composition with thickening agents, in a concentration from 0.5 to 5.0% by weight. State of the art thickeners with bicarbonate and zinc salts include, but are not limited to chicle, xantham, arabic, karaya or tragacanth gums. Alginates, carrageenans and cellulose derivatives such as sodium carboxymethyl, methyl, or hydroxy ethyl compounds as appropriate for the intended preparations, surfactants and abrasives may also be included. Alcohols will otherwise be avoided for their known risk factor for oral cancers. In order to decrease dental cavities and add flavor, without using metabolizable sugars, sweetening agents as saccharin, sodium cyclamate, sorbitol, aspartamane and others may be used in concentrations from 0.005 to 5.0% by weight of the total composition, albeit xylitol, vide supra, is preferred.

Lactilol may also be used as a substitute for sucrose in our sugar-free compositions. Lactilol is a disaccharide sugar alcohol derived from lactose, highly water soluble and of low hygroscopicity, making it a suitable non-caloric sweetener for use in solid dosage forms.

A number of compounds may be added to the various liquid compositions of this invention in order to enhance the aromas or tastes of these preparations. These substances may also impart fragrances to the aforementioned. Grapefruit and citrus aroma and flavors have been included in smoking tobacco articles both prior to smoking and on smoking in both the main stream and the side stream smokes. Methyl phenyl pentanol derivatives have been used to augment and enhance aromas, such as in perfumes and colognes. Schreck patented these derivatives for use in tobaccos and tobacco articles in U.S. Pat. No. 4,458,699 (Jul. 10, 1994) which is herein incorporated by reference. Floral, green, weedy, fruity, minty, citrusy, oriental and green pepper-like aroma and taste nuances are well known to those skilled in the art of flavors and fragrances for such compositions as in oral sprays, mouthwashes, mouth rinses, gels, dentifrices and other medicinal, nutritional or breath freshener products.

Wahl and co-workers at the National Institutes of Health taught methods to treat chronic inflammatory diseases in U.S. Pat. No. 5,499,688 (Sep. 12, 1995), which is herein incorporated by reference. They administered effective amounts of nitric oxide scavengers to decrease the amount of putative nitric oxide present at the site of the inflammation. These compounds belonged to complexes with L-arginine, L-canavanine, citrulline and amino guanidine. They note, akin to the argument herein favoring the use of antioxidants to neutralize free radicals. This '688 patent augurs a method for treating gingivitis and periodontitis. Kleinberg in U.S. Pat. No. RE31181 (Mar. 15, 1983), which is also herein incorporated by reference, also teaches arginine and arginine peptides for oral care preparations.

Over the centuries, Chinese herbalists have identified individual herbs that have either beneficial effects on the human body or even therapeutic properties. The National Institute of Health has recently established an agency for research in these so-called alternative therapies.

Oral-based preparations have been composed to exert local effects in the mouth or for providing herbal extracts for buccal absorption and then exert their systemic effects, depending on the specific herbal properties.

Since individual herb compositions when swallowed may be destroyed by gastric acid or digested by enzymes in the gut, herbal based products have also been prepared as gels and toothpastes, such as proposed in U.S. Pat. No. 5,466,443 by Ho (Nov. 14, 1995) which is herein incorporated by reference. Dr. Ho proposed the delivery of these herbs by oral retention bases, as chicle or gels so that these herbal extracts are then absorbed through the buccal mucosa.

It is preferred that the antioxidants of the present invention be provided in a form which is as pure as possible. They should be present without noxious lubricants (sand, soaps, talc), fillers, colors, binders, dispersants or like adjuvants sometimes employed as delivery excipients in the aerosol pharmaceutical industry. The intra-oral sprays and mouth-washes may, however, and preferably will contain breath fresheners and/or flavors. The antioxidant ingredients, as well as other ingredients in the formulations, will be administered in combination to exert their synergistic and therapeutic effects; however, for convenience and dosage consistency, as well as for assisting in the uniform administration of various dosages of the individual ingredients throughout the day it is advantageous that the ingredients described herein be administered together, either in their usual chemical composition or protected in encapsulating forms such as lecithin liposomes or other oral delivery vehicles as are known in the industry.

Intra-oral sprays are well known to those familiar with the art of this industry. These intra-oral sprays are prepared in vials of variable sizes and milliliter concentrations which contain accordingly a predetermined number of metered sprays from non-aerosol pumps or with propellants for aerosol sprays. Dosages will depend on product compositions and labeled so that a predetermined number of sprays equals one daily dose. The preparations will be sprayed directly into the mouth at recommended intervals during the day. Other intra-oral preparations which may include flavors are presented as concentrated breath sprays. In administering the present invention, one would spray directly into the mouth for breath freshening action and intra-oral absorption of vitamins and antioxidants. These intra-oral sprays with vitamins and synergistic antioxidants may be labeled according to FDA regulations as dietary supplements because of rapid buccal absorption of these nutrients.

Carriers for the active ingredients of this patent may be included, but are not limited to such solid delivery systems as oral gels, powders and toothpastes. The compositions of these are conventional bases and well known to those skilled in the manufacture of these products. Toothpaste base, for example, may include but is not limited to ingredients as calcium diphosphate, methyl cellulose, saccharin, glycerine, chlorophyll, sodium lauryl sulphate and others. These may also include abrasives for the teeth such as sodium bicarbonate, flavoring agents, as mints, and fluorides to prevent tooth decay. Gum bases include those of arabic, guar and others as already noted.

The sulphur-containing amino acid cysteine is one of the three amino acid constituents of the tripeptide antioxidant glutathione. Studies have shown that cysteine and cysteine derivatives, such as N-acetylcysteine, as presented in U.S. Pat. No. 4,910,222 by Puricelli, have bronchial liquefying and expectorating properties. These compounds may be administered orally as a solid (capsules) or as a liquid (emulsions). Other routes of administration include rectally (suppositories) or by inhalation (nebulizers and aerosols). In the latter method, the posologic units for inhalation are between 5.0 and 500 mg of the active substance. In the compositions of the present application, these may be administered in vehicles as oral liposomes.

Various products may be administered to reduce the viscosity of mucin in sputum. Productive cough is a common symptom. Mucus in the respiratory tract, especially in chronic tobacco smokers as well as other conditions including cystic fibrosis, may be treated with cough syrups and expectorants. Ceramin and Tabachnik described the use of reducing sulfhydryl compounds to decrease the sputum viscosity in patients with pneumonia, chronic bronchitis and cystic fibrosis in U.S. Pat. No. 4,424,216 (January, 1984), which is herein incorporated by reference. They proposed as the preferred sulfhydryl agent WR 2721 to be given orally in capsules of gelatin so that in vivo it may then release free sulfhydryl groups.

As noted in this present application, cough suppressants, bronchodilators as well as agents like cysteine, arginine, methionine, taurine, vitamin A and others to reduce mucin viscosity may be added to these compositions. The latter will make sputum more liquid and easier to expectorate for these patients and for chronic tobacco abusers. U.S. Pat. No. 4,927,850, herein incorporated by reference, described methionine in oral or parenteral preparations for ameliorating inflammatory symptoms of respiratory diseases.

As an optional embodiment, the compositions herein described with synergistic antioxidants to combat free radicals in the oropharynx may also contain zinc or zinc compounds. The state of the art of oral care and hygiene has long recognized the value of zinc to neutralize oral malodor and the value of zinc ions for their anti-plaque and anti-calculus properties. Mouth rinses, mouthwashes, gels and dentifrices will thus complement the properties of the xylitol sweetener in oral and dental preventative care.

Various patents have described different zinc compounds and other complexes in oral compositions. Domke and Bergman taught an aqueous zinc-polyamide complex as a solution for control of halitosis, dental care and to decrease the astringency and metallic taste of zinc in the mouth in U.S. Pat. No. 5,587,147 (Dec. 24, 1996), which is herein incorporated by reference. This patent discloses previous documents dealing with zinc salts such as zinc chloride, zinc phenol sulfonate, zinc citrate and other zinc complexes, some of which purportedly also exhibit oral antimicrobial activities. The zinc ion concentrations in these compositions will be at least 0.1 to 3.0 weight percent and these will preferably be in an alkaline pH to avoid demineralization of tooth enamel at acid levels. In any event, these aqueous compositions will not have a pH below 6, and preferably about 7.

Another method of application of the active ingredients in the orally sprayed products is to incorporate the various antioxidants, minerals and amino acids in liposomes or other state of the art encapsulating vehicles, akin to nanospheres, glycospheres and others as used also in topical compositions. Liposomes are lecithin spheres that form an oil protective membrane around the putative active ingredients of the composition. These carriers also deliver the active ingredients locally for their preventive and therapeutic functions as well as systemically through buccal mucosal absorption. Unger and co-workers, in U.S. Pat. No. 5,580,575 (Dec. 3, 1996), which is herein incorporated by reference, have taught therapeutic drug delivery systems comprising gas-filled liposomes which encapsulate the active preparation. Earlier, Chakrabarti and associates, in U.S. Pat. No. 5,380,531 (Jan. 10, 1995), which is also herein incorporated by reference, disclosed preparations comprising a lipid and a modified peptide for similar uses of amino acids and peptides into liposomes. Knight et al. (U.S. Pat. '388) has taught about small particle aerosol liposomes and liposome combinations for medical delivery uses.

Other preparations which are optionally included in this invention involve applications for intranasal sprays and for vapor inhalers and humidifiers. These may include additional compounds known to decrease the swelling of the mucosa of the nostrils and paranasal sinuses due to the common cold, hay fever and upper respiratory allergies or sinusitis.

There are a number of "steam inhalers" on the market, whereby an aqueous solution with these water dissolvable antioxidant molecules may be administered. Some contraptions are contoured to the face so that a mild cloud of steam at various gradations may be delivered for periods of five to up to 30 minutes.

The synergistic antioxidants of this invention used with the steam are useful as an adjunct to preventing and ameliorating free radical photodamage, tobacco smoke damage (the so-called "smoker's face") or other environmental pollutants or chemicals. Facial steamers are also of utility to prepare skin for cosmetic products for skin care, as the steam mist cleanses and moisturizes. Steam inhalers containing the present antioxidant complex with cysteine may be used as well for temporary relief of the symptoms of colds or allergy by directing the cloud of steam to the nasal passages and oral cavity and there combating the free radicals engendered by the ailment, the allergic antigens or the pollutants, including tobacco smoke. These compositions too may be delivered in protective carriers as liposomes.

Examples of presenting the composition include high concentrations delivered by "dropper" or directly by a fixed dose spray or tube to 1½–4 oz. of tap or distilled water. This solution is then placed in the receptacle of the heating unit to administer the steam as an inhaler and/or as a skin care product. Alternatively, these compositions may be packaged in water soluble pouches. The unit-of-use pouch is made from a water soluble film, which will hold a specific amount of the complex as a powder as a pre-measured dosage form. The individual pouch will be measured depending on the amount of liquid to be used in the specific steam inhaler, humidifier, or oral irrigator mechanism. This dose will also depend on the time of use of the steam, such as the facial steam inhalers for 5 to 30 minutes.

Aerosols are classically defined as particles or droplets, ranging from 0.15 to 5 micron in size, which are suspended or dispersed in a gaseous media. More currently, the term aerosol has been expanded to include products which are pressure-dispensed as liquid or semi-solid streams, mists, fairly dry to wet sprays, powders, and even foams. Aerosol technology is well established to those familiar with the state of the art in this industry and there is vast literature on the containers, method of dispensing and testing the physico-chemical and toxicological properties of both the aerosol system and the propellants. A number of approved commercial concerns for preparation and testing of these aerosols are in business. These companies are also approved for manufacturing medicinal metered dose inhalers and aerosol pharmaceuticals, abiding also to the regulations of the Federal Environmental Protection Agency.

Aerosol products, as proposed herein, may employ hydrocarbons as the propellants, replacing the now much restricted chlorofluoracarbons. The aerosol products are generally hermetically sealed so that the contents cannot leak, spill or become contaminated. The packages are tamper proof and deliver the intended preparations in an efficient manner with little waste to the selected sites, such as the oropharynx and the upper respiratory tract. By control of spray pattern, particle size, and volume delivered per time, the product is thus applied directly to its intended destination without contact by the user.

All aerosols consist of a product concentrate, propellant, container and valve. The concentrate contains the active ingredients and necessary solvents and fillers. Appropriate propellants and valve systems need be considered due to solvency and viscosity of the concentrate. In contrast, in order to deliver a spray as for intra-oral or intra-nasal or oro-pharyngeal compositions, a homogenous solution is prepared, which also includes the propellant and the solvents. In these cases, propellants are likely selected from alcohols, acetone or glycols.

In aerosol medical preparations, metered-dose valves permit delivery of exact drug dosage of the active ingredient (s) to the oro-pharynx, wherein these may both act locally as well as systemically following buccal absorption. As an example, inhalers prescribed for patients with asthma produce a fine mist which has access to the oro-respiratory mucosa. The rate of spray is also determined by the propellant, the solvent used and the valve and vapor pressure. Spray dryness or wetness and droplet size depend on propellant concentration.

There are two types of oral sprays that administer the active ingredients into the mouth or under the tongue (sublingual sprays). The latter are used mainly for dispensing low molecular drugs, such as nitro-glycerine, with demonstrated adequate transmucosal absorption.

Oral sprays are mainly marketed as mouth fresheners. As noted, this system must be soluble in vehicle and propellant and be therapeutically effective at low dosages. There are also a variety of novel delivery systems via aerosols and pumps. Aerosol systems diminish the loss of the active medication through volatization from non aerosol containers.

In summary, for the topical administration to the mucosal surfaces of the oro-pharyngeal and upper respiratory tract, direct delivery systems are preferred. These include but are not limited to intra-oral sprays, mists, metered dose inhalers, nebulizers, aerosols, and others. In this manner the specific synergistic antioxidants, vitamins, and minerals plus other substances such as flavorings, fragrances or breath fresheners may be added as indicated for each specific putative use.

Mist aerosols may be present as the complex of the present invention can be dissolved in non-aqueous lipophilic readily volatile solvents. A carrier gas can be employed, or a dispersion or an emulsion prepared in water. Aqueous mixtures of physiologically compatible liquids in the carrier gas are contemplated.

Other delivery techniques for spray or aerosol distribution of these products for the purposes so intended and described include so-called pump atomizers. By means of a piston pump mechanism in the spray head, an excess pressure is generated in the atomizer vessel, resulting in the active liquid complex of this invention being forced through the atomizer jet and distributed in the surrounding air. Aerosol propellant gas packs include liquid gas systems and two phase aerosols where the propellant gas in the pressure container is both in the liquid and gaseous phase, as well as others, including suspension aerosols and pressurized gas systems, well known in the industry as state of the art delivery systems as described by Biesalski, H. K., in U.S. Pat. No. 5,112,598 issued on May 12, 1992 and herein incorporated by reference. Thus, the pharmaceutical preparations of the present invention are dissolved or dispersed in a non-toxic medium. The solution or dispersion can be atomized via an aerosol, whereby it is distributed in extremely fine particles in a carrier gas, such as in aerosol propellant gas packs, pump aerosols or devices which exact individual dosages, such as liquid misting and solid atomizing devices, as are well known in the art of this industry.

The prevention and amelioration of free radical damage in the oro-pharynx and upper respiratory tract requires the presence of an effective antioxidant system. The response of the mucosa to the oxidative tissue damage is inflammation and exudation of plasma engendering one or more oral or respiratory tract signs and symptoms. The body's endogenous antioxidants are called on to neutralize free radicals.

The literature cites various studies where low levels of an antioxidant have been supplemented by oral or parenteral routes. Examples of increasing vitamin C blood levels in smokers have been cited. The oro-pharyngeal mucosa may receive these antioxidants in the form of intra-oral sprays, mists, inhalers, humidifiers and nebulizers. Spray droplets via inhalation tend to accumulate in the upper respiratory tract. Sanchez and Handler in U.S. Pat. No. 5,461,080 issued Oct. 24, 1995, the disclosure of which is incorporated by reference, provide airborne protectants against oxidative tissue damage by vapor phase phenolic antioxidants. These components of the gas mixture may be administered by various therapeutic breathing devices.

An intra-oral composition is provided in a spray container with a pump mechanism (no aerosol or propellants). The label will carry the list of ingredients with measured amounts expressed as micrograms or milligrams per measured dose. The label will carry the words nutrient or nutritional spray or dietary supplement, complying with the FDA dietary regulations of the Health and Education Act of 1994. Ingredients will conform to official compendia, including the U.S. Pharmacopeia and the Homeopathic Pharmacopeia of the United States. All the ingredients are generally regarded as safe. The active ingredients will be complemented by flavors and an artificial sweetener, which also prevents development of dental plaque and cavities.

The intra-oral spray will be administered by the user 2 to 3 sprays 3 to 4 times per day. An example of a suitable package could be 0.45 fl. oz. vial containing a fixed number of metered sprays, (240). The preparation will serve to prevent free radical damage in the mouth and throat caused by tobacco and other pollutants. Absorption of the vitamins and antioxidants though the lining of the mouth will occur as dietary supplements for the body's metabolic needs. The spray will serve to freshen the breath and aid in mouth hygiene, including the use of the sweetener xylitol, with its aforementioned beneficial effects.

This composition may be administered by a pump atomizer such as a piston pump mechanism. By this mechanism in the spray head an excess pressure is generated in the atomizer vessel containing the solution or dispersion with the active complex, which forces the liquid through the atomizer. The minute, finely distributed particles in the spray liquid may then reach their targets in the oral cavity. Measured doses will be calculated, such that an X number of sprays per day would deliver a total of the following synergistic antioxidants.

EXAMPLE 1

An intra-oral spray of the following composition was prepared as follows:

| | |
|---|---|
| L-glutathione | 20 mg. |
| selenomethionine | 40 mcgm. |
| ascorbic acid | 60 mg. |
| alpha tocopherol | 30 I.U. |
| L-cysteine | 10 mgm. |
| vitamin A | 500 I.U. |
| zinc gluconate | 15 mg. |

The artificial sweetener xylitol and flavors, as discussed, were added, such as peppermint oil or citrus group to aid as a breath freshener. The active ingredients alone or in combination were administered in liposomes, as already stated above.

EXAMPLE 2

The following composition was prepared in aerosol propellent gas packs, as are well known in the art of this industry. These aerosols delivered finely distributed minute particles with the active complex on the oro-pharyngeal mucosa. These mist aerosols contained the active substance liquid in the carrier gas as follows:

| | |
|---|---|
| L-glutathione | 20 mg. |
| selenium | 50 mcgm. |
| ascorbic acid (vitamin C) | 60 mgm. |
| alpha-tocopherol (vitamin E) | 30 I.U. |
| L-cysteine | 20 mg. |
| xylitol | 10 mg. |
| zinc glutonate | 15 mg. |

The formulation is calculated to deliver predetermined amounts per day, as pumps are designed to give fixed amounts per spray (metered dose applicators). The delivery mechanism is by a pump or mist type or by aerosol with corresponding propellants, typically isobutane, I 134 and others, but not by chlorofluorocarbons.

The active ingredients are dissolved in water and any other necessary solvent such as glycerine for those compositions which may have other ingredients as complementary to the active complex. As noted, these active ingredients may be encapsulated each alone or in combination in protective delivery vehicles as oral liposomes. Examples include the fat soluble vitamin A or to correspond to minimum daily requirements, such as a retinol equivalent of 1000 mcgms. Vitamin A may also be administered as carotenoids or as beta carotene (120 mcgm). Zinc gluconate or acetate 15 mg. and vitamin D-3 (cholecalciferol) with the appropriate calcium and magnesium salts may be added. Various natural antioxidants may form part of these intra-oral sprays and include but not restricted to proanthocyanidins (20 mgs. per day) from pine bark or grape seeds, Japanese green tea's catechins and xanthines, as well as bioflavonoids, rose hips or acerola. Novel herbal preparations may also be included, such as gingko biloba, echinacea and others known in health care and naturotherapy fields.

These intra-oral spray or mouthwash preparations will be sweetened with artificial sweeteners, such as xylitol, for its beneficial oral properties (vide supra). In these compositions, such as breath fresheners, appropriate flavors will be added, as herein described.

As noted, other ingredients may be added to the aerosol compositions of this invention depending upon an intended clinical use. Without being bound to any particular theory, to combat free radicals in the oro-pharynx and upper respiratory tract of smokers, these intra-oral spray compositions might be coupled with standard expectorants, reducers of mucin viscosity, bronchodilators and taurine, for smokers with hoarseness, asthma, bronchitis or other pulmonary airway conditions aggravated by cigarette smoke and requiring bronchial dilation to reduce bronchospasm and ameliorate associated symptoms such as wheezing, coughing and shortness of breath. Compounds that reduce mucin viscosity, such as L-cysteine, are other additives.

The synergistic antioxidant complex of this application may also be incorporated in comestible units which disperse in the mouth. One such process was taught by Cherukuri and co-workers in U.S. Pat. No. 5,587,182 (Dec. 24, 1996), which is herein incorporated by reference.

There are a number of mouthwash and rinse preparations in use for oral and dental care, including oral hygiene, odor prevention and local therapy. Some deal with specific targets, such as combating oral micro-organisms with suitable antibacterials or preventing tooth decay and promoting dental care. These mouthwashes are usually aqueous-alcoholic preparations with specific antimicrobials or fluorides, as described in U.S. Pat. Nos. 4,923,685 (May 8, 1990) by Wuelknitz et al. and 3,975,513 (Aug. 17, 1976) by Weisz, respectively, which are both herein incorporated by reference.

Mouthwashes are either clear or opaque, ready-to-use solutions, which may be colored and flavored. Some may be used undiluted and some are solid as concentrates or powders which have to be proportionately diluted with water before use. Oral compositions for use herein may also be used in the form of gels, such as described in U.S. Pat. No. 5,372,802 (Dec. 13, 1994) by Barrows et al., or dentifrice compositions such as are well known in the art of the industry and described by U.S. Pat. No. 5,348,734 (Sep. 20, 1994) by Ratcliff, both of which are herein incorporated by reference.

The term mouthwash includes compositions wherein medicinal products may be included for specific oro-pharyngem and odontologic conditions and are medically referred to as mouth rinses. Examples would include an anti-microbial agent such as those for treatment of oral candidiasis (thrush) or corticosteroid for mouth rinses for management of oro-pharyngeal ulcers as both occur in patients with AIDS. In these oral conditions, and particularly in patients with AIDS and their opportunistic infections, free radical species are indeed pathogenetic. Patients infected with HIV tend to have subnormal levels of GSH in plasma, in extracellular fluids, and intracellularly. GSH depletion of CD-4 cells in these patients augurs for poor survival. Thus, it becomes imperative to replenish GSH in patients with HIV-AIDS by supplementation with GSH or the pro-drugs cysteine or N-acetylcysteine locally for better defenses, as proposed by the compositions of this invention as well as systemically by oral administration. Thus, mouth rinses, as well as intra-oral sprays with these compositions provide significant adjunct therapies in the management of these oral conditions, particularly in symptomatic patients with HIV and AIDS.

EXAMPLE 3

The following composition was prepared as a mouthwash for oral administration of the active antioxidants as contemplated herein (expressed in % by weight):

| | |
|---|---|
| water | balance |
| SD alcohol | 4.00 |
| ascorbic acid | 1.00 |
| alpha tocopherol | 0.75 |
| carrot oil | 0.10 |
| selenomethionine | 0.20 |
| calcium gluconate | 0.25 |
| L-glutathione | 0.10 |
| xylitol-sweetener | 7.00 |
| coloring agents | 0.20 |
| flavoring | 0.50 |

EXAMPLE 4

In an attempt to reduce tobacco, alcohol and other pollutant induced free radical damage to the oral cavity, a preferred embodiment of this patent contemplates a mouthwash preparation without alcohol. Similarly, it would not contain free sugars or saccharin as sweeteners, but would contain a polyol sweetener like the aforementioned xylitol for its beneficial properties to the mouth, gums and teeth. Such a composition was prepared as follows (expressed in % by weight):

| | |
|---|---|
| L-glutathione | 0.10 |
| selenomethionine | 0.05 |
| L-ascorbic acid | 1.0 |
| alpha tocopherol | 0.75 |
| green tea extract | 0.05 |
| xylitol sweetener | 9.25 |
| flavoring agent (peppermint oil) | 1.0 |

Vegetable oils as sesame, cassia, pistachio, apricot kernel oil, glycerin and others may be used for flavoring and body. Aloe vera and agave juice are ingredients for their soothing properties and beneficial effects. Astringents as non-alcoholic witch hazel may be included as well as other antimicrobials, antibacterial enzymes, celluloses and non-ionic surfactants such as poloxalens, as is well known in the art of this industry.

EXAMPLE 5

The following composition was prepared for administering the active ingredients as a gel (expressed as % by weight):

| | |
|---|---|
| glycerin | 42.0 |
| poloxamer | 18.0 |
| ascorbic acid | 2.0 |

| | |
|---|---|
| sodium lauryl sulfate | 1.2 |
| natural peppermint oil | 1.0 |
| alpha tocopherol | 0.75 |
| green tea | 0.5 |
| calcium lactate | 0.25 |
| selenomethionine | 0.20 |
| sodium fluoride | 0.20 |
| L-glutathione | 0.10 |
| coloring agent | 0.10 |
| deionized water | balance |
| xylitol sweetener | 15.00 |
| zinc acetate | 0.15 |

As optional embodiments of the compositions of this invention, other ingredients may be added as breath fresheners and breath cleansing (anti-halitosis) agents. Plevy taught in U.S. Pat. No. 4,740,368 (Apr. 26, 1988), which is herein incorporated by reference, compositions with amylase as breath cleansing confections. Alpha amylases are synthesized by the salivary glands and exocrine pancreas and are able to digest carbohydrates. Plevy's preparation used 1-8-SKB units of alpha-amylase of fungal origin to degrade starch. Along with artificial sweeteners and flavoring, this enzyme was the main ingredient of comestible confectionary bases, such as gums or lozenges. Separately, Pera in U.S. Pat. No. 4,775,525 (Oct. 4, 1988), which is also herein incorporated by reference, taught a dental formulation containing sodium alginate. It is used as a calcium chelating agent which weakens the bond between the plaque and the teeth. He advocated the concomitant use of benzalkonium chloride and zinc.

Oral irrigators squirt a stream of pulsating water out of a nozzle or tip. Irrigators are effective at removing food debris, germs, and bacteria in areas not accessible to the toothbrush or by flossing. Plaque is a sticky material made of the aforementioned with saliva attached to teeth at and below the gum line. Mineralized plaque is called calculus. Both are hard to remove because of their location but irrigators like hydrofloss using irrigators with magnetic devices show a greater than 40% reduction in calculus volume. Plaque and calculus are responsible for gum diseases. Irrigators are also adjuncts in therapy of gingivitis and periodontitis. Electric toothbrushes do not replace oral irrigators. Free radicals are generated during the inflammatory reactions secondary to plaque causing gingivitis. Oral irrigators, as part of this treatment, have reservoirs wherein mouth rinses, two to three capfuls, may be added as part of the irrigation process. The mouth rinses of this invention with its synergistic antioxidant complex plus the artificial sugar, xylitol, which reduces numbers of putative oral bacteria, streptococcus and reduces plaque formation, may be used in these oral irrigators, like hydrofloss. Additional compositions would include a mouth rinse concentrate in such manner that this complex with xylitol in 10 cc individual packets may be prepared to add to the water in the reservoir so that the antioxidants are additional therapies to the pulsating irrigating water of these apparati, as taught in U.S. Pat. No. D 372,778 by Wa Brunson (Aug. 13, 1996), which is herein incorporated by reference.

EXAMPLE 6

A concentrate of the active ingredients of this invention was prepared for administration by a glass dropper having a 4 to 6 drop reservoir per application. The concentrate was of the following composition (expressed as % by weight):

| | |
|---|---|
| L-glutathione | 0.2 |
| L-selenomethionine | 0.05 |
| ascorbyl palmitate | 2.00 |
| L-cysteine | 0.10 |
| vitamin E acetate | 1.00 |
| vitamin A | 0.50 |
| green tea extract | 0.50 |
| zinc acetate | 0.25 |

Glycerin as solvent and xylitol as sweetener and dental protectants were also added. The concentrate was administered in deiodinized water by dropper added to the water reservoir of an oral irrigator.

There are other dental and oral hygiene products which can be used herein. For example, some ingredients contain sialogogue for treatment of erostomia and for gum disease. Kleinberg taught in U.S. Pat. No. 5,078,129 (Jan. 7, 1992) a device to stimulate saliva as an organic acidulant, a food grade sweetener, and calcium phosphate. The same inventor, in U.S. Pat. No. RE31181 (Mar. 15, 1983) also taught a means and method for improving natural defenses against dental caries using arginine containing peptides, which, of course, may be used with these and other devices. as are known in the industry. The synergistic antioxidant with the xylitol sweetener complex of this invention may be added alone or in combination with aforementioned sialogogue, anti-microbials, fluorides and others for their specific and beneficial therapeutic effects in the oral cavity.

The active ingredients of this invention may also be incorporated with peroxygen oral hygiene products, including tooth whitening systems, dentifrices, mouthwashes and oral rinses. Persalt compounds may include sodium perborate monohydrate or sodium carbonate perohydrate. These will include typical dentifrice formulations as abrasives, which clean and polish teeth, such as calcium or magnesium carbonate or calcium phosphate, binders and thickeners such as gums or carboxymethylcellulose, surfactants, humectants such as PEG or glycerin and preservatives. The peroxides will generate bubbles for improving dentifrice cleaning action combined with antioxidants to neutralize free radicals in oral cavities.

Standard toothpaste formulations may be used with the addition of the active ingredient antioxidants of this patent, as such or as encapsulated in protective liposomes. The base formulations to be used are standard state of the art in this industry and, as noted, may contain fluorides and zinc salts. The dentifrices of this invention will be used by the consumer wishing to decrease within the oral cavity, including the gums, free radicals created from tobacco or other sources. The dentifrice will be used in the usual manner on a toothbrush or applied to the gums by various techniques.

EXAMPLE 7

The following composition (expressed as % by weight) was used as a dentifrice:

| Ingredient | & By Weight |
|---|---|
| water | balance |
| glycerol | 32.0 |
| magnesium carbonate | 3.5 |
| sodium fluoride | 3.5 |
| zinc acetate | 0.50 |
| L-glutathione | 0.1 |

-continued

| Ingredient | & By Weight |
|---|---|
| L-selenomethionine | 0.05 |
| ascorbic acid | 1.50 |
| N-acetylcysteine | 0.10 |
| vitamin E | 0.25 |
| benzalkonium chloride | 0.10 |
| polyvinyl pyrrolidone | 7.5 |
| xylitol as sweetener | 0.25 |
| coloring agent | 0.20 |
| flavor, as peppermint | 0.20 |

Ascorbic acid or ascorbyl palmitate may be incorporated in protective liposomes, as well as the glutathione and cysteine, N-acetyl cysteine and/or other amino acids employed in dentifrice formulations. As noted, whitening agents such as sodium monofluorophosphate and anti-microbials may also be comprised in these dental formulations.

I claim:

1. A method for reducing free radical damage induced by tobacco products and environmental pollutants comprising administering in a suitable carrier in concentrations for effectively reducing said free radical damage to the oro-pharynx and upper respiratory tract of a user a combination of from 0.01 and 10% (weight) glutathione, from 1.0 to 25% (weight) ascorbic acid, from 0.001 to 10% (weight) of a source of selenium and from 0.001 to 2.0% (weight) of a sulphur containing amino acid.

2. The method of claim 1 wherein said combination and carrier are introduced to the oro-pharynx and upper respiratory tract of a user by use of an intranasal vapor inhaler or humidifiers, steam inhalers or oral dental irrigators.

3. The method of claim 1 wherein said combination and carrier are introduced to the oro-pharynx and upper respiratory tract of a user by use of an intra-oral spray.

4. The method of claim 1 wherein said combination and carrier are introduced to the oro-pharynx and upper respiratory tract of a user by use of an aerosol.

5. The method of claim 1 wherein said combination and carrier are introduced to the oro-pharynx and upper respiratory tract of a user by use of a stream inhaler, nebulizer or vaporizer.

6. The method of claim 1 wherein said source of selenium comprises a member selected from the group consisting of elemental selenium and selenomethionine.

7. The method of claim 1 wherein said sulphur containing amino acid comprises a member selected for the group consisting of L-cysteine and L-methionine.

8. The method of claim 1 wherein said combination further comprises between 0.1 and 5.0% (weight) D, L-alpha tocopherol acetate based upon the total weight of said combination.

* * * * *